United States Patent [19]

Moriwaki et al.

[11] Patent Number: 5,286,858
[45] Date of Patent: Feb. 15, 1994

[54] OPTICALLY ACTIVE THIENOTRIAZOLODIAZEPINE COMPOUNDS

[75] Inventors: Minoru Moriwaki, Oita; Syuji Yuasa, Fukuoka; Hiroyuki Kitani; Michio Terasawa, both of Oita, all of Japan

[73] Assignee: Yoshitomi Pharmaceutical Industries, Ltd., Osaka, Japan

[21] Appl. No.: 774,945

[22] Filed: Oct. 11, 1991

[30] Foreign Application Priority Data

Oct. 12, 1990 [JP] Japan .................. 2-274451
Jul. 31, 1991 [JP] Japan .................. 3-214512

[51] Int. Cl.$^5$ .................. C07D 495/12; C07D 495/14
[52] U.S. Cl. .................................................. 540/560
[58] Field of Search .................. 540/560; 514/220

[56] References Cited

U.S. PATENT DOCUMENTS

| | | | |
|---|---|---|---|
| 4,820,703 | 4/1989 | Tahara et al. | 514/220 |
| 4,937,240 | 6/1990 | Moriwaki et al. | 514/220 |
| 5,104,543 | 3/1992 | Brandt et al. | 540/560 |

FOREIGN PATENT DOCUMENTS

| | | | |
|---|---|---|---|
| 0315698 | 5/1989 | European Pat. Off. | C07D 495/14 |
| 0320992 | 6/1989 | European Pat. Off. | |
| WO88/09333 | 1/1988 | PCT Int'l Appl. | 540/560 |

OTHER PUBLICATIONS

Burger, *Medicinal Chemistry*, 3rd ed. (1970), Part I, p. 81.

*Primary Examiner*—Mukund J. Shah
*Assistant Examiner*—Philip I. Datlow
*Attorney, Agent, or Firm*—Sughrue, Mion, Zinn, Macpeak & Seas

[57] ABSTRACT

Stable crystals of an acid addition salt of an optically active thienotriazolodiazepine compound or its hydrate of the formula

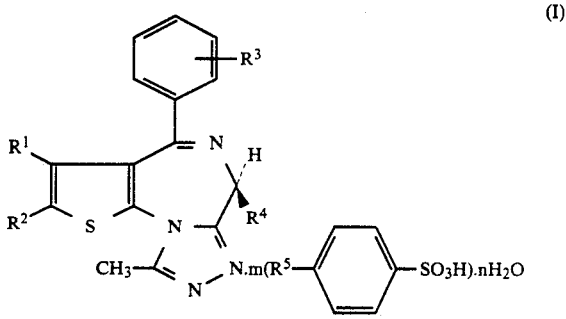

wherein $R^1$ is hydrogen, $R^2$ is 2-phenylethyl substituted by alkyl having 1 to 5 carbon atoms, 2-morpholinocarbonylethyl or alkyl having 6 to 12 carbon atoms, or $R^1$ and $R^2$ may combinedly form a saturated 5-membered ring having one substituent selected from the group consisting of morpholinomethyl, morpholinocarbonyl and N,N-dipropylcarbamoyl, $R^3$ is halogen, alkyl having 1 to 5 carbon atoms or alkoxy having 1 to 5 carbon atoms, $R^4$ is trifluoromethyl or alkyl having 1 to 5 carbon atoms, $R^5$ is hydrogen or methyl, m is 1-2, and n is 0-2. The present invention provides optically active thienotriazolodiazepine compounds having strong PAF-antagonistic activity as markedly stable crystals which are excellent in crystalline property, permit purification by recrystallization, and have high chemical purity and optical purity, thereby rendering industrial large-scale synthesis attainable. In addition, crystallization thereof facilitates medicinal standardization and pharmaceutical formulation.

5 Claims, No Drawings

OPTICALLY ACTIVE THIENOTRIAZOLODIAZEPINE COMPOUNDS

BACKGROUND OF THE INVENTION

The present invention relates to stable crystals of acid addition salts of optically active thienotriazolodiazepine compounds, which have antagonistic activity on platelet-activating factor and are useful as pharmaceuticals.

Ever since Benbeniste et al found a factor capable of strongly aggregating platelets [platelet-activating factor (PAF)] from rabbit basocytes in 1972, the physiological roles of PAF have been investigated, and it has been clarified that PAF is a factor for various physiological reactions including platelet aggregation, hypotension, acute allergy, smooth muscle contraction, inflammation, pain, edema, as well as disorders in respiratory, cardio-vascular and venous systems in living bodies.

Accordingly, a compound having PAF-antagonistic activity is considered to be extremely useful for various PAF-induced diseases including inflammations, allergies, anaphylactic shocks, septic shocks, vascular diseases such as DIC (disseminated intravascular coagulation), myocardinal diseases, asthma, pulmonary edema, and adult respiratory diseases, and many studies of substances having antagonistic action against physiological activity of PAF have been under way.

The present inventors invented compounds having extremely strong PAF-antagonistic activity; for example, (±)-4-(2-chlorophenyl)-2-(2-(4-isobutylphenyl)ethyl)-6,9-dimethyl-6H-thieno[3,2-f][1,2,4]triazolo[4,3-a][1,4]diazepine (hereinafter referred to as Compound A, U.S. Pat. No. 4,820,703) of the following formula

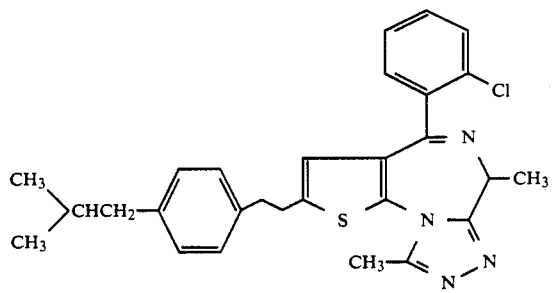

and (±)-3-[4-(2-chlorophenyl)-6,9-dimethyl-6H-thieno[3,2-f][1,2,4]triazolo[4,3-a][1,4]diazepin-2-yl]propionic acid morpholide (hereinafter referred to as Compound B, U.S. Pat. No. 4,937,240) of the following formula

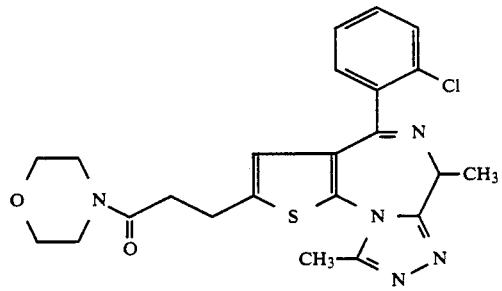

These Compounds A and B possess strong PAF-antagonistic activity and are useful as PAF-antagonists. These Compounds have an asymmetric carbon at the 6-position, and an isomer whose absolute configuration is an S-configuration has several times stronger PAF-antagonistic activity than Compounds A and B (racemates), and is low toxic with less effect on the central nervous system. Furthermore, since the isomer is effective by oral administration and long-lasting, it is more useful as a pharmaceutical.

However, these optically active isomers of Compound A and Compound B, having an S-configuration could be obtained only as an amorphous by a conventional purification method (e.g. column chromatography, recrystallization), and large-scale synthesis and purification thereof have been extremely difficult, causing many problems in terms of purification and physicochemical properties which are important for medicinal standardization and pharmaceutical formulation. Thus, obtaining them as stable crystals has been the major object in developing them as pharmaceuticals.

SUMMARY OF THE INVENTION

With the aim of solving the above-mentioned problems, the present inventors have made an attempt to crystallize the above-mentioned optically active isomers of Compounds A and B having an S-configuration by forming an acid addition salt, and made intensive studies of crystallization using inorganic or organic acids such as hydrochloric acid, sulfuric acid, hydrobromic acid, maleic acid, fumaric acid, malic acid, tartaric acid, succinic acid and methanesulfonic acid, but such studies have hardly succeeded. Finally, however, the present inventors have found that an acid addition salt with very superior crystalline property can be obtained with p-toluenesulfonic acid or benzenesulfonic acid. The crystals of the acid addition salt with p-toluenesulfonic acid or benzenesulfonic acid are stable, have superior reproducibility, and permit industrial large-scale synthesis. In addition, the PAF-antagonistic activity is no less inferior to that of the amorphous compounds. Thus, the present invention provides crystalline thienotriazolodiazepine compounds having markedly high chemical purity and optical purity, by which the problems as described have been solved.

That is, the present invention provides:

(1) stable crystals of an acid addition salt of an optically active thienotriazolodiazepine or its hydrate of the formula

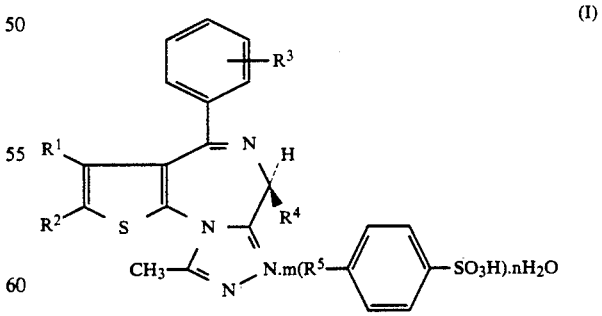

wherein $R^1$ is hydrogen, $R^2$ is 2-phenylethyl substituted by alkyl having 1 to 5 carbon atoms, 2-morpholinocarbonylethyl or alkyl having 6 to 12 carbon atoms, or $R^1$ and $R^2$ may combinedly form a saturated 5-membered ring having one substituent selected from among morpholinomethyl, morpholinocarbonyl and N,N- dipropylcarbamoyl, $R^3$ is halogen, alkyl having 1 to 5 carbon atoms or alkoxy having 1 to 5 carbon atoms, $R^4$ is trifluoromethyl or alkyl having 1 to 5 carbon atoms, $R^5$ is hydrogen or methyl, m is 1-2, and n is 0-2;

(2) stable crystals of an acid addition salt of an optically active thienotriazolodiazepine or its hydrate of the formula

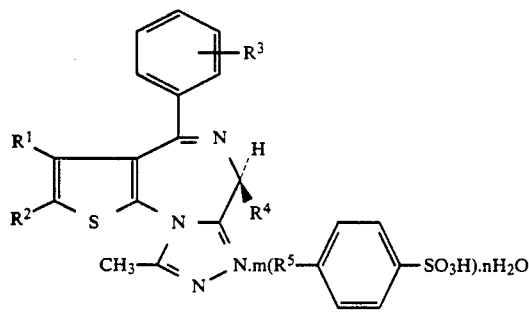

(I)

wherein each symbol is as defined in (1) above, which is obtained by reacting an optically active thienotriazolodiazepine compound of the formula

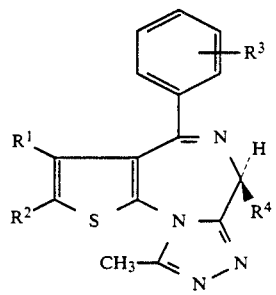

(II)

wherein each symbol is as defined in (1) above, with an acid of the formula

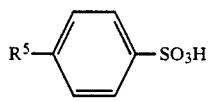

(III)

wherein $R^5$ is as defined in (1) above, or its hydrate;

(3) stable crystals as described in (1) above wherein $R^3$ is chlorine and $R^4$ is methyl; and (4) stable crystals as described in (1) above wherein $R^1$ is hydrogen, $R^2$ is 2-(4-isobutylphenyl)ethyl or 2-morpholinocarbonylethyl, $R^3$ is chlorine and $R^4$ is methyl.

DETAILED DESCRIPTION OF THE INVENTION

More specifically, the present invention provides stable crystals of the following Compounds 1, 2 and 3.

Compound 1: 6S-(—)-4-(2-chlorophenyl)-2-(2-(4-isobutylphenyl)-ethyl)-6,9-dimethyl-6H-thieno[3,2-f][1,2,4]triazolo[4,3-a]-[1,4]diazepine p-toluenesulfonate

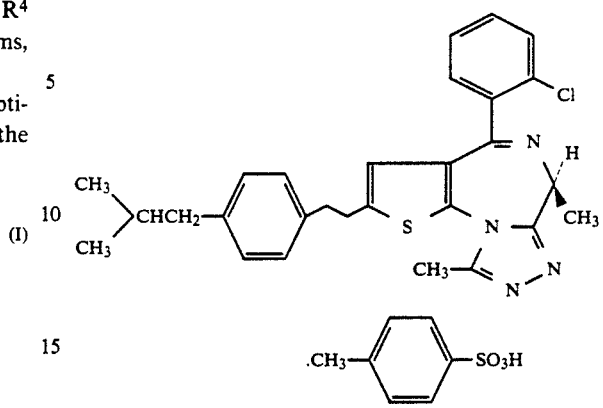

Compound 2: 6S-(—)-3-[4-(2-chlorophenyl)-6,9-dimethyl-6H-thieno[3,2-f][1,2,4]triazolo[4,3-a][1,4]diazepin-2-yl]propionic acid morpholide 3/2 p-toluenesulfonate 3/2 hydrate

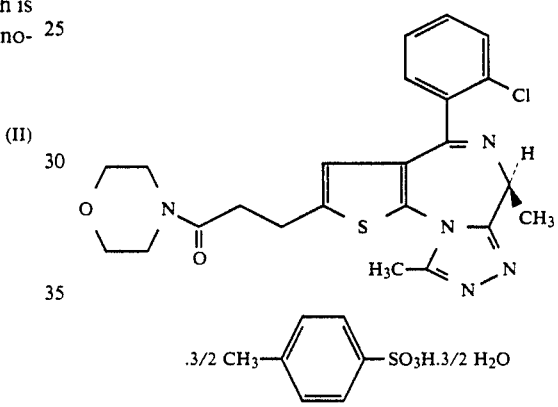

Compound 3: 6S-(—)-3-[4-(2-chlorophenyl)-6,9-dimethyl-6H-thieno[3,2-f][1,2,4]triazolo[4,3-a][1,4]diazepin-2-yl]propionic acid morpholide 3/2 benzenesulfonate 3/2 hydrate

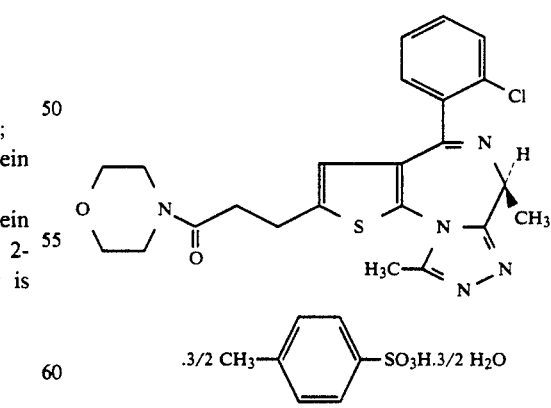

In formula (I) above, the 2-phenylethyl substituted by alkyl having 1 to 5 carbon atoms is 2-(4-methylphenyl)ethyl, 2-(4-isopropylphenyl)ethyl, 2-(4-butylphenyl)ethyl, 2-(4-isobutylphenyl)ethyl, 2-(4-pentylphenyl)ethyl, 2-(4-isopentylphenyl)ethyl, or the like. The alkyl having 6 to 12 carbon atoms is hexyl, heptyl, octyl, nonyl, decyl, undecyl and dodecyl. The saturated 5-membered ring having one substituent selected from among morpholinomethyl, morpholinocarbonyl and N,N-dipropylcarbamoyl which is formed combinedly together by $R^1$ and $R^2$ stands for the following.

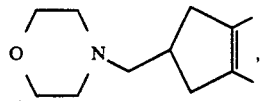

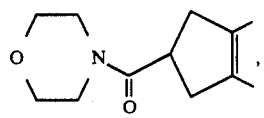

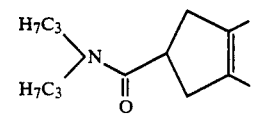

Halogen means chlorine, bromine, fluorine or iodine, alkyl having 1 to 5 carbon atoms means methyl, ethyl, propyl, isopropyl, butyl, isobutyl, tert-butyl, pentyl or isopentyl, and alkoxy having 1 to 5 carbon atoms means methoxy, ethoxy, propoxy, isopropoxy, butoxy, isobutoxy, tert-butoxy or pentyloxy. As the acid addition salt, there may be specifically mentioned salts with benzenesulfonic acid or p-toluenesulfonic acid, m means 1, 3/2 or 2, and n means 0, ½, 1, 3/2 or 2.

The synthetic intermediates of the optically active compound of formula (II) can be synthesized in the following manner. That is, an optically active intermediate compound of the formula

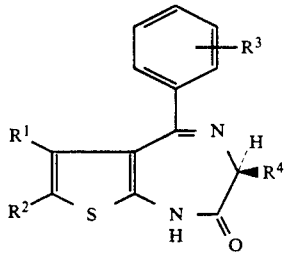

(d)

wherein $R^1$, $R^2$, $R^3$ and $R^4$ are as defined above, can be obtained by reacting a compound of the formula

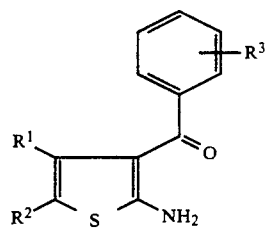

(a)

wherein each symbol is as defined above, with a halide compound wherein the nitrogen atom is protected which is represented by the formula

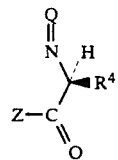

(b)

wherein Z is halogen, Q is a nitrogen-protecting group and $R^4$ is as defined above, to obtain a compound of the formula

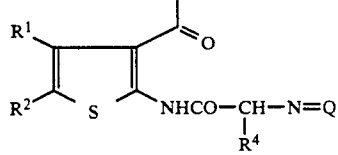

(c)

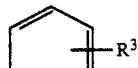

wherein each symbol is as defined above, removing the protecting group is give a primary amine compound, and subjecting the compound obtained to dehydrocyclization.

In the above formulae, halogen means chlorine, bromine, iodine, or the like, and examples of the protecting group represented by —N=Q include phthalimido, 3,4-diphenylmaleimido, succinimido, and the like.

The reaction between the compounds of formulae (a) and (b) is carried out by refluxing under heating for 1 to 3 hours in a solvent such as chloroform, methylene chloride, dichloroethane or tetrahydrofuran.

The protecting group for the compound of formula (c) can be removed by refluxing under heating for 1 to 5 hours in methanol, ethanol, isopropyl alcohol or butanol with the addition of hydrazine monohydrate with or without further addition of conc. hydrochloric acid. The compound of formula (d) can be obtained by dehydrocyclization in a solvent (e.g. ethanol, propanol, isopropyl alcohol, butanol, benzene, toluene, dimethylformamide, dimethylacetamide) preferably in the presence of a weak acid catalyst such as acetic acid, propionic acid or silica gel at room temperature or under heating.

By treating the thus-obtained compound of formula (d) by the method described in U.S. Pat. Nos. 4,820,730, 4,937,240 and so on, there can be obtained an optically active compound of formula (II) as a non-crystalline powder.

The thus-obtained non-crystalline powder of the compound of formula (II) is dissolved in methanol, ethanol, isopropyl alcohol, ethyl acetate, isopropyl ether or a mixed solvent thereof, to which is added 1-2 equivalents of p-toluenesulfonic acid monohydrate or benzenesulfonic acid monohydrate in ethanol, methanol, isopropyl alcohol, ethyl acetate, isopropyl ether or a mixed solvent thereof, and the mixture is allowed to stand. The resulting crystals are recrystallized from ethanol, methanol, isopropyl alcohol, isopropyl ether or a mixed solvent thereof to give stable crystals having high optical purity, of the acid addition salts of the optically active compounds of the present invention or hydrates thereof.

The existence ratio of the optical isomer was estimated by high performance liquid chromatography and its optical purity is shown as e.e.

The PAF-antagonistic activity of the compounds of the invention was examined through inhibitory effects on PAF-induced lethal shock in mice, in accordance with the Young et al method [Prostaglandins, Vol. 30, 545 (1985)]. As a result, it was found that Compound 1 and Compound 2 of the invention showed about three times stronger antagonistic activity on PAF than their racemates.

The acute toxicity of the compounds of the invention was examined with the use of 6 male mice. The test compound was orally administered at a dose of 1000 mg/kg, and the mice were kept under observation for 5 days. No death was observed.

The acid addition salts of the optically active thienotriazolodiazepine compounds of the invention exhibit several times stronger PAF-antagonistic activity than the existing racemic compounds, and the activity is long-lasting. Furthermore, since the toxicity of the present compounds is low and they exhibit substantially no depressive effects on the central system such as sedative action nor muscle relaxation activity, they are useful as safe PAF-antagonistic medicaments.

In view of the above facts, the compounds of the present invention are useful as PAF-antagonists, and are preventable or treatable of various kinds of PAF-induced diseases such as inflammations, allergies, anaphylactic shocks, septic shocks, myocardiac diseases, asthma, pulmonary edema and adult respiratory diseases.

The compounds of the present invention can be safely administered orally or parenterally to human beings in the form of the pharmaceutical composition such as tablets, pills, powder, capsules, granules, solutions, inhalants, suppositories, percutaneous absorbable preparations or injectable solutions. The pharmaceutical composition can be prepared by, for example, mixing a therapeutically effective amount of at least one compound with a pharmaceutically acceptable additive such as an excipient, an extender, a diluent or a solubilizer.

The dose may vary depending upon the compound selected or employed, the severity of patients to be treated and the age of patients, but the daily dose for human adults preferably ranges from 0.1 to 100 mg in single or multiple doses.

(1) Tablets

A composition of 0.5 part of the compound of Example 1, 25 parts of lactose, 35 parts of crystalline cellulose and 3 parts of corn starch is mixed well, and kneaded with binder prepared by 2 parts of corn starch. The paste is passed through a 16 mesh sieve and dried in an oven at 50° C., and forced through a 24 mesh sieve. The powder thus obtained, 8 parts of corn starch, 11 parts of crystalline cellulose and 9 parts of talc are mixed well and the mixture is compressed with a punch into tablets containing 0.5 mg of active ingredient.

(2) 1% Powder

A composition of 1 part of the compound of Example 1 and 90 parts of lactose is mixed well and kneaded with binder prepared by a suitable amount of methylcellulose. The mixture is passed through a 16 mesh sieve and dried in an oven at 50° C. The dried granules are forced through 32 mesh sieve with pressure and mixed with a suitable amount of silicon dioxide to produce 1% powder.

The optically active thienotriazolodiazepine compound of the above-described formula (II) having strong PAF-antagonistic activity has been so far obtained only as a non-crystalline powder (amorphous). On the contrary, the present invention provides same as markedly stable crystals [formula (I)] which show excellent crystalline property, permit purification by recrystallization, and have high chemical purity and optical purity, thereby rendering industrial large-scale synthesis attainable. In addition, crystallization thereof facilitates medicinal standardization and pharmaceutical formulation.

Also, conversion into p-toluenesulfonate or benzenesulfonate resulted in 3–4 times improved absorption in living bodies as compared with racemates.

Furthermore, by using the crystalline acid addition salts of the invention, crystallization of the compounds as free base or its hydrate can be achieved. In addition, it has become attainable to introduce the crystalline hydrochloride. The detailed description in connection with this point is given in Examples 4 and 5 to be mentioned below.

The present invention is hereinbelow described in detail by illustrating reference examples and working examples to which the present invention is not limited.

Note that in reference examples and working examples, the optical purity (e.e.) of the product was determined by high performance liquid chromatography using a chiral cell OD column (Daiseru Kagaku Kogyo) with a mixed solution of n-hexane and isopropyl alcohol (9:1) as a moving phase. S-Configuration was confirmed by X-ray diffraction.

Reference example 1

To a solution of 75 g of crude 2-amino-3-(2-chlorobenzoyl)-5-(2-(4-isobutylphenyl)ethyl)thiophene prepared by the method as described in U.S. Pat. No. 4,820,703 in 500 ml of chloroform was added 50 g of N-phthalyl-L-alanylchloride with stirring and the mixture was refluxed for 3 hours. After cooling, the mixture was washed with an aqueous sodium hydrogencarbonate solution, dried over anhydrous sodium sulfate, filtered off and concentrated under reduced pressure. The resulting oil was chromatographed on a silica gel column and crystallized from ethanol to give 26.7 g of (−)-3-(2-chlorobenzoyl)-5-(2-(4-isobutylphenyl)ethyl)-2-(N-phthalyl-L-alanyl)aminothiophene, melting at 103°–106° C.

$[\alpha]_D^{25}$ −37.0° (c=2, chloroform)

$^1$H-NMR (CDCl$_3$) δ: 0.82 (3H), 0.92 (3H), 1.92 (3H), 2.40 (2H), 2.86 (4H), 5.23 (1H), 6.26 (1H), 7.00 (4H), 7.20–7.96 (8H), 11.0–11.2 (1H)

Reference example 2

To a suspension of 18.0 g of the compound obtained in the above Reference example 1 in 250 ml of ethanol was added 1.5 g of hydrazine monohydrate with stirring under ice-cooling and the mixture was stirred for 1.5 hours keeping the temperature below 0° C. To the mixture was added 70 ml of isopropyl ether and the precipitated crystals were collected by filtration. To a suspension of 12 g of the obtained crystals in 250 ml of methanol was added 7 ml of conc. hydrochloric acid with stirring at room temperature. The mixture was heated at 60° C. with mantle heater with stirring and further stirred under heating for 2 hours. After cooling, the resultant mixture was concentrated in vacuo. To the residue was added 700 ml of chloroform and insoluble material was filtered off.

The chloroform solution was washed with a 5% aqueous sodium hydrogencarbonate solution, dried over anhydrous magnesium sulfate and concentrated in vacuo. To a solution of the resulting oil in 250 ml of isopropyl alcohol was added 4.9 g of acetic acid and the mixture was refluxed under heating for 20 hours. After cooling, the mixture was concentrated in vacuo and the residue was dissolved in 300 ml of chloroform. The solution was washed with a 5% aqueous sodium hydrogencarbonate solution, and dried over anhydrous magnesium sulfate, and the filtrate was concentrated in vacuo. To the residue was added 40 ml of isopropyl ether and the crystals began to precipitate. After allowing to stand overnight, the precipitated racemate was filtered off and the filtrate was concentrated in vacuo to give 2.0 g of 3S-(−)-5-(2-chlorophenyl)-7-(2-(4-isobutylphenyl)-ethyl)-1,3-dihydro-3-methyl-2H-thieno[2,3-e][1,4]diazepin-2-one as an oil.

>99% e.e.;

$[\alpha]_D^{23} - 14.8°$ (c=2, chloroform)

$^1$H-NMR (CDCl$_3$) δ: 0.84 (3H), 0.92 (3H), 1.76 (3H), 2.42 (2H), 2.08–2.96 (4H), 3.96 (1H), 6.18 (1H), 7.00 (4H), 7.20–7.42 (4H), 8.60–8.78 (1H)

Reference example 3

To a solution of 1.6 g of the compound obtained in Reference example 2 in 40 ml of chloroform was added 1.63 g of phosphorus pentasulfide with stirring at room temperature. The mixture was refluxed under heating with stirring for an hour. After cooling, the mixture was washed with a 5% aqueous sodium hydrogencarbonate solution and dried over anhydrous magnesium sulfate. The filtrate was concentrated in vacuo. The resulting oil was chromatographed on a silica gel column with chloroform-methanol (100: 0–3) as the eluent and the eluate of the objective fractions was concentrated in vacuo and the residue was crystallized from isopropyl ether to give 0.81 g of 3S-(−)-5-(2-chlorophenyl)-7-(2-isobutylphenyl)ethyl)-1,3-dihydro-3-methyl-2H-thieno[2,3-e][1,4]diazepine-2-thione as yellow crystals melting at 191°–193° C.

>99.5% e.e.;

$^1$H-NMR (CDCl$_3$) δ: 0.85 (3H), 0.92 (3H), 1.95 (3H), 1.90 (1H), 2.44 (2H), 2.84–2.98 (4H), 4.18 (1H), 6.20 (1H), 7.00 (4H), 7.20–7.42 (4H)

Reference example 4

To a solution of 0.52 g of the thione compound obtained in Reference example 3 in 15 ml of tetrahydrofuran was added 0.11 g of hydrazine monohydrate with stirring at room temperature and further stirred at room temperature for 2 hours. The mixture was concentrated in vacuo and to the residue was added 40 ml of toluene. The solution was dried over anhydrous magnesium sulfate. To the filtrate was added 0.54 g of triethyl orthoacetate and stirred under heating at 80° C. with stirring for an hour. After cooling, the resultant mixture was concentrated in vacuo and the residue was chromatographed on a silica gel column with chloroform-methanol (100: 1–3) as the eluent and the eluate of the objective fractions was concentrated in vacuo. To the resulting oil was added 5 ml of isopropyl ether and the solution was allowed to stand overnight. The precipitated racemate was filtered off and the filtrate was concentrated in vacuo to give 0.32 g of 6S-(−)-4-(2-chlorophenyl)-2-(2-(4-isobutylphenyl)ethyl)-6,9-dimethyl-6H-thieno[3,2-f][1,2,4]triazolo[4,3-a][1,4]diazepine as an amorphous powder.

>99.5% e.e.;

$[\alpha]_D^{23.5} - 56.2°$ (c=1, chloroform)

$^1$H-NMR (CDCl$_3$) δ: 0.84 (3H), 0.92 (3H), 1.90 (1H), 2.08 (3H), 2.44 (2H), 2.64 (3H), 2.80–3.20 (4H), 4.36 (1H), 6.36 (1H), 7.04 (4H), 7.20–7.46 (4H)

Example 1

To a solution of 10.2 g of amorphous powdery 6S-(−)-4-(2-chlorophenyl)-2-(2-(4-isobutylphenyl)ethyl)-6,9-dimethyl-6H-thieno[3,2-f][1,2,4]triazolo[4,3-a][1,4]diazepine obtained in Reference example 4 in 255 ml of ethyl acetate was added a solution of 3.97 g of p-toluenesulfonic acid monohydrate in 51 ml of ethanol and the solution was allowed to stand. After the resulting crystals were air-dried, the crystals were recrystallized from 40 ml of ethanol to give 10.1 g of 6S-(−)-4-(2-chlorophenyl)-2-(2-(4-isobutylphenyl)ethyl)-6,9-dimethyl-6H-thieno[3,2-f][1,2,4]triazolo[4,3-a][1,4]diazepine p-toluenesulfonate as colorless crystals, melting at 189.3° C.

>99.5% e.e.;

$[\alpha]_D^{25} - 116.3°$ (c=1, methanol)

$^1$H-NMR (CDCl$_3$) δ: 0.86 (3H), 0.92 (3H), 2.10 (3H), 2.30 (3H), 2.46 (2H), 2.82–3.10 (4H), 3.00 (3H), 4.56 (1H), 6.40 (1H), 6.90–7.74 (12H), 12.00–12.44 (1H)

The procedure of this example was carried out three times and the quality of each lot was tested for standardization. Since each lot showed almost constant values, it turned out that compounds having stable quality could be obtained by means of this invention (Table 1).

According to the simplified stability tests of 60° C., 4 weeks; 40° C., 6 months; and 40° C., 6 months under 75% humidification, there were no changes in their appearance, contents and TLC.

Further, a single and stable crystalline compound was ascertained by X-ray diffraction patterns of each lot (Table 2).

TABLE 1

| Test item | Lot No. 1 | Lot No. 2 | Lot No. 3 |
| --- | --- | --- | --- |
| Appearance | White crystalline powder | White crystalline powder | White crystalline powder |
| Smell | non | non | non |
| NMR | In accordance with standard spectrum | In accordance with standard spectrum | In accordance with standard spectrum |
| IR | In accordance with standard spectrum | In accordance with standard spectrum | In accordance with standard spectrum |
| UV (λmax) | 244 nm | 244 nm | 244 nm |
| MS (m+) | 488 | 488 | 488 |
| Specific rotation | −117.3° | −116.3° | −116.1° |
| Melting point (°C.) | 189.6 | 189.3 | 189.5 |
| Solution | yellow and clear | yellow and clear | yellow and clear |
| DSC | 191.9° | 191.5° | 191.8° |

TABLE 1-continued

| Test item | Lot No. 1 | Lot No. 2 | Lot No. 3 |
| --- | --- | --- | --- |
| Specific volume (rough) | 3.47 | 3.52 | 4.58 |
| Specific volume (dense) | 1.95 | 1.97 | 1.91 |
| Particle size | 5.2 μm | 4.3 μm | 3.6 μm |
| X-ray diffraction | crystals | crystals | crystals |

TABLE 2

| No. | Diffraction angle 2θ (°) | d (Å) | Relative intensity $I/I_1$ (%) |
| --- | --- | --- | --- |
| 1 | 26.168 | 3.4025 | 57 |
| 2 | 18.904 | 4.6904 | 71 |
| 3 | 17.061 | 5.1927 | 75 |
| 4 | 14.513 | 6.0981 | 41 |
| 5 | 11.260 | 7.8513 | 39 |
| 6 | 5.568 | 15.8579 | 100 |

[X-ray apparatus: CU—Kα, graphite monochromator, 40 KV, 40 mA]

Reference example 5

To a solution of 45.3 g of methyl 3-(5-amino-4-(2-chlorobenzoyl-2-thienyl)propionate prepared by the method described in U.S. Pat. No. 4,937,240 in 400 ml of chloroform was added 42.6 g of N-phthalyl-L-alanyl chloride with stirring and refluxed under heating for 3 hours. After cooling, the mixture was washed with a 5% aqueous sodium hydrogencarbonate solution, dried over anhydrous magnesium sulfate, filtered off, and the filtrate was concentrated in vacuo. The resulting oil was crystallized from isopropyl ether to give 70.8 g of methyl (−)-3-[4-(2-chlorobenzoyl)-5-N-phtalyl-L-alanylamino-2-thienyl]propionate, melting at 124°–126° C.

$[\alpha]_D^{25} -36.7°$ (c=1, chloroform)
$^1$H-NMR (CDCl$_3$) δ: 1.92 (3H, d), 2.57 (2H, t), 2.96 (2H, t), 3.64 (3H, s), 5.23 (1H, q), 6.39 (1H, s) 7.1–7.96 (8H, m), 12.27 (1H, broad)

Reference example 6

To a suspension of 19.6 g of the compound obtained in Reference example 5 in 400 ml of methanol was added 5.5 g of 100% hydrazine monohydrate with stirring under ice-cooling and further stirred at 0° C. for 1.5 hours. To the solution was added 30 ml of isopropyl ether and the precipitated crystals were collected by filtration. To the suspension of 17 g of the resulting crystals in 300 ml of methanol was added 11 ml of conc. hydrochloric acid under ice-cooling and the mixture was refluxed under heating for an hour. After cooling, the reaction mixture was concentrated in vacuo and the resulting oil was dissolved in 200 ml of chloroform. The solution was washed with a 5% aqueous sodium hydrogencarbonate solution, dried over anhydrous magnesium sulfate, and concentrated in vacuo.

To a solution of the resulting oil in 200 ml of isopropyl alcohol was added 2.3 g of acetic acid and the mixture was refluxed under heating for 20 hours.

After cooling, the reaction mixture was concentrated in vacuo and the resulting oil was dissolved in 200 ml of chloroform. The solution was washed with a 5% aqueous sodium hydrogencarbonate solution, dried over anhydrous magnesium sulfate and concentrated in vacuo. The residue was chromatographed on a silica gel column with a mixed solvent of chloroform-methanol (100:0.5) as the eluent. The eluate of the objective fractions was concentrated in vacuo and to the residue was added 25 ml of ethyl acetate to precipitate crystals. After allowing to stand overnight, the precipitated racemate was filtered off and the filtrate was concentrated in vacuo to give 4.66 g of 3S-(+)-methyl 3-[5-(2-chlorophenyl)-3-methyl-1,3-dihydro-2-oxo-thieno[2,3-e][1,4]diazepin-7-yl]propionate as an amorphous powder.

>99% e.e.;
$[\alpha]_D^{25} +7.3°$ (c=1, chloroform)
$^1$H-NMR (CDCl$_3$) δ: 1.76 (3H, d), 2.58 (2H, t), 2.97 (2H, t), 3.64 (3H, s), 3.93 (1H, q), 6.24 (1H, s) 7.08–7.5 (4H, m), 9.16 (1H, broad)

Reference example 7

To a solution of 4.6 g of the compound obtained in Reference example 6 in 100 ml of chloroform was added 2.8 g of phosphorus pentasulfide and the mixture was refluxed under heating with stirring for an hour. After cooling, the mixture was washed with a 5% aqueous sodium hydrogencarbonate solution and dried over anhydrous magnesium sulfate, and then the filtrate was concentrated in vacuo. The resulting oil was chromatographed on a silica gel column with chloroform-methanol (100:0-1) as the eluent and the eluate of the objective fractions was concentrated in vacuo to give about 3.2 g of methyl 3-[5-(2-chlorophenyl)-3-methyl-1,3-dihydro-2-thioxothieno[2,3-e][1,4]diazepin-7-yl]propionate. To a solution of the thione compound in 100 ml of methanol was added 1 g of 100% hydrazine monohydrate and the mixture was stirred at room temperature for an hour. After the reaction mixture was concentrated in vacuo, the resulting oil was dissolved in 100 ml of toluene and the solution was dried over anhydrous magnesium sulfate, and then filtered. To the filtrate was added 4.8 g of triethyl orthoacetate and stirred at 70° C. for 4 hours, and then concentrated in vacuo. The residue was chromatographed on a silica gel column with a mixed solvent of chloroform and methanol (100:1–100:3) as the eluent. The eluate of the objective fractions was concentrated in vacuo and to the residue was added 10 ml of isopropyl ether to precipitate crystals. After allowing to stand overnight, the precipitated racemate was filtered off and the filtrate was concentrated in vacuo to give 1.68 g of 6S-(−)-methyl 3-[4-(2-chlorophenyl)-6,9-dimethyl-6H-thieno[3,2-f][1,2,4]triazole[4,3-a][1,4]-diazepin-2-yl]propionate.

>99% e.e.;
$[\alpha]_D^{25} -35.6°$ (c=1, chloroform)
$^1$H-NMR (CDCl$_3$) δ: 2.1 (3H, d), 2.65 (2H, t), 2.71 (3H, s), 3.09 (2H, t), 3.68 (3H, s), 4.33 (1H, q) 6.43 (1H, s), 7.2–7.6 (4H, m)

Reference example 8

To a solution of 1.6 g of the compound obtained in Reference example 7 in 20 ml of methanol was added 0.32 g of potassium hydroxide under ice-cooling and the mixture was stirred at room temperature for 1.5 hours. After the mixture was concentrated in vacuo, to the residue was added 20 ml of water and the solution was adjusted to pH 3 with a dilute hydrochloric acid. The liberating carboxylic acid compound was extracted with chloroform and the extract was washed with brine, and then dried over anhydrous magnesium sulfate. The solution was concentrated in vacuo to give 0.71 g of 6S-(−)-3-[4-(2-chlorophenyl)-6,9-dimethyl-6H-thieno[3,2-f][1,2,4]triazolo[4,3-a][1,4]diazepin-2-yl]propionic acid as an amorphous powder.

>99% e.e.;

$[\alpha]_D^{25} -39.5°$ (c=1, chloroform)

¹H-NMR (CDCl₃) δ: 2.07 (3H, t), 2.5–2.8 (5H, m), 3.08 (2H, t), 4.34 (1H, q), 6.45 (1H, s), 7.2–7.5 (4H, m), 7.5–7.8 (1H, broad)

Reference example 9

To a solution of 0.61 g of the compound obtained in Reference example 8, 0.21 g of 1-hydroxybenzotriazole hydrate and 0.16 g of morpholine in 20 ml of dimethylformamide was added 0.37 g of dicyclohexylcarbodiimide and the mixture was stirred at room temperature for 20 hours. After the resultant mixture was concentrated in vacuo, the residue was dissolved in 50 ml of chloroform. The solution was washed with a 5% aqueous sodium hydrogencarbonate solution and then water, and dried over anhydrous magnesium sulfate. After the solution was concentrated in vacuo, the residue was chromatographed on a silica gel column with a mixed solvent of chloroform and methanol (100: 1–3) as the eluent. The eluate of the objective fractions was concentrated in vacuo and to the residue was added 5 ml of isopropyl ether, and then the solution was allowed to stand overnight. The precipitated racemate was filtered off and the filtrate was concentrated in vacuo to give 0.38 g of 6S-(−)-3-[4-(2-chlorophenyl)-6,9-dimethyl-6H-thieno[3,2-f][1,2,4]triazolo[4,3-a][1,4]diazepin-2-yl]propionic acid morpholide as an amorphous powder.

>99% e.e.;

$[\alpha]_D^{25} -33.4°$ (c=1, chloroform)

¹H-NMR (CDCl₃) δ: 2.04 (3H, d), 2.62 (2H, t), 2.7 (3H, s), 3.14 (2H, t), 3.3–3.8 (8H, m), 4.32 (1H, q), 6.44 (1H, s), 7.2–7.6 (4H, m)

Example 2

To a solution of 2.86 g (6.30 mmol) of amorphous powdery 6S-(−)-3-[4-(2-chlorophenyl)-6,9-dimethyl-6H-thieno[3,2-f][1,2,4]triazolo[4,3-a][1,4]diazepin-2-yl]propionic acid morpholide obtained in Reference example 9 in 3 ml of ethanol were added a solution of 2.16 g (11.3 mmol×1.8 equivalent) of p-toluenesulfonic acid monohydrate in 2.1 ml of ethanol and 5.1 ml of isopropyl ether, and the solution was allowed to stand at room temperature for 3 days to precipitate crystals. To the solution was added two volumes of isopropyl ether little by little, and the solution was allowed to stand for about 24 hours to precipitate 4.1 g (36%) of crude crystals. To a solution of the resulting crude crystals in 40 ml of thermal ethanol was added 40 ml of isopropyl ether. After cooling, to the solution was added further two volumes of isopropyl ether and the mixture was allowed to stand for about 24 hours. The precipitated crystals were collected by filtration to give 2.05 g of 6S-(−)-3-[4-(2-chlorophenyl)-6,9-dimethyl-6H-thieno[3,2-f][1,2,4]-triazolo[4,3-a][1,4]diazepin-2-yl]propionic acid morpholide 3/2 p-toluenesulfonate 3/2 hydrate, melting at 157.0° C.

99.5% e.e.;

$[\alpha]_D^{25} -38.2°$ (c=0.86, chloroform)

Example 3

To a solution of 22.6 mg (0.129 mmol) of amorphous powdery 6S-(−)-[4-(2-chlorophenyl)-6.9-dimethyl-6H-thieno[3,2-f][1,2,4]-triazolo[4,3-a][1,4]diazepin-2-yl]propionic acid morpholide obtained in Reference example 9 in 0.05 ml of ethanol were added a solution of 45.5 mg (0.258 mmol×2.0 equivalent) of benzenesulfonic acid monohydrate in 0.05 ml of ethanol and 0.1 ml of isopropyl ether, and the solution was allowed to stand at room temperature for about 15 hours. Further, to the solution was added two volumes of isopropyl ether, and the solution was allowed to stand for about 10 days. The precipitated crystals were collected by filtration to give 26.0 mg (76%) of 6S-(−)-3-[4-(2-chlorophenyl)-6,9-dimethyl-6H-thieno[3,2-f][1,2,4]triazolo[4,3-a][1,4]diazepin-2-yl]propionic acid morpholide 3/2 benzenesulfonate 3/2 hydrate, melting at 158.0° C.

99.5% e.e.

Example 4

6S-(−)-4-(2-Chlorophenyl)-2-[2-(4-isobutylphenyl)ethyl]-6,9-dimethyl-6H-thieno[3,2-f][1,2,4]triazolo[4,3-a][1,4]diazepine p-toluenesulfonate (13.2 g) obtained in Example 1 was suspended in 50 ml of toluene. The suspension was washed with an aqueous sodium hydrogencarbonate solution, washed with water, and the toluene layer was dried over magnesium sulfate. After concentration, 10.5 g of the resulting oil was dissolved in 100 ml of isopropyl ether and the mixture was ice-cooled. The precipitated crystals were filtered off and the filtrate was dried under reduced pressure to give 2.6 g of 6S-(−)-4-(2-chlorophenyl)-2-[2-(4-isobutylphenyl)ethyl]-6,9-dimethyl-6H-thieno[3,2-f][1,2,4]triazolo[4,3-a][1,4]diazepine ½ hydrate as a white crystalline powder, melting at 59°–60° C.

>99.5% e.e.;

$[\alpha]_D -94.7°$ (c=1, methanol)

¹H-NMR (CDCl₃) δ: 0.88 (6H, d, J=6.8 Hz), 1.55–2.07 (1H, m), 2.07 (3H, d, J=6.8 Hz), 2.43 (2H, d, J=6.8 Hz), 2.64 (3H, s), 2.74–2.96 (4H, m), 4.31 (1H, q, J=6.8 Hz), 6.33 (1H, s), 7.00 (4H, s), 7.2–7.5 (4H, m)

Anal. Calc. C₂₈H₂₉ClN₄S ½ H₂O: C, 67.52; H, 6.07; N, 11.25 Found: C, 67.63; H, 6.06; N, 11.25 MS m/z: 488

In the same manner, there can be obtained crystals from a hexane solution.

Example 5

6S-(−)-4-(2-Chlorophenyl)-2-[2-(4-isobutylphenyl)ethyl]-6,9-dimethyl-6H-thieno[3,2-f][1,2,4]triazolo[4,3-a][1,4]-diazepine p-toluenesulfonate (162 g) obtained in Example 1 was suspended in 500 ml of toluene. The suspension was neutralized with an aqueous sodium hydrogencarbonate solution. The toluene layer was separated, washed with water, and dried over magnesium sulfate. After concentration, the resulting oil was dissolved in 300 ml of ethanol, and the mixture was stirred with ice-cooling. To the mixture was added 21.6 ml of conc. hydrochloric acid. The mixture was concentrated, and then added with 1 l of ethyl acetate for crystallization. The precipitated crystals were filtered off and the filtrate was dried under reduced pressure to give 56.4 g of 6S-(−)-4-(2-chlorophenyl)-2-[2-(4-isobutylphenyl)ethyl]-6,9-dimethyl-6H-thieno[3,2-f]-[1,2,4]triazolo[4,3-a][1,4]diazepine hydrochloride as a pale yellow crystalline powder, melting at 112°–114° C.

>99.5% e.e.;

$[\alpha]_D -139.9°$ (c=1, methanol)

¹H-NMR (CDCl₃) δ: 0.89 (6H, d, J=6.8 Hz), 1.54-2.06 (1H, m), 2.1 (3H, d, J=6.8 Hz), 2.42 (2H, d, J=6.8 Hz), 2.7-3.2 (7H, m), 4.55 (1H, q, J=6.8 Hz), 6.38 (1H, s), 7.0 (4H, s), 7.2-7.6 (4H, m) 9.8-10.3 (1H, broad)

What is claimed is:

1. Stable crystals of an acid addition salt of an optically active thienotriazolodiazepine compound or its hydrate of the formula

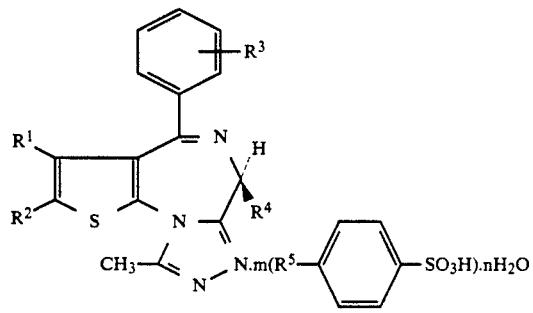

wherein R¹ is hydrogen, R² is 2-(4-isobutylphenyl)ethyl or 2-morpholinocarbonylethyl, R³ is chlorine, R⁴ is methyl, R⁵ is hydrogen or methyl, m is 1-2, and n is 0-2.

2. Stable crystals according to claim 1, which is 6S-(−)-4-(2-chlorophenyl)-2-(2-(4-isobutylphenyl)ethyl)-6,9-dimethyl-6H-thieno[3,2-f][1,2,4]triazolo[4,3-a][1,4]diazepine p-toluenesulfonate.

3. Stable crystals according to claim 1, which is 6S-(−)-3-[4-(2-chlorophenyl)-6,9-dimethyl-6H-thieno[3,2-f][1,2,4]triazolo[4,3-a][1,4]diazepin-2-yl]propionic acid morpholide 3/2 p-toluenesulfonate 3/2 hydrate.

4. Stable crystals according to claim 1, which is 6S-(−)-3-[4-(2-chlorophenyl)-6,9-dimethyl-6H-thieno[3,2-f][1,2,4]triazolo-[4,3-a][1,4]diazepin-2-yl]propionic acid morpholide 3/2 benzenesulfonate 3/2 hydrate.

5. Stable crystals according to claim 1, which is 6S-(−)-4-(2-chlorophenyl)-2-(2-(4-isobutylphenyl)ethyl)-6,9-dimethyl-6H-thieno[3,2-f][1,2,4]triazolo[4,3-a][1,4]diazepine p-toluenesulfonate, showing the following x-ray diffraction pattern:

| No. | Diffraction angle | | Relative intensity |
| --- | --- | --- | --- |
|  | 2θ (°) | d (Å) | I/I₁ (%) |
| 1 | 26.168 | 3.4025 | 57 |
| 2 | 18.904 | 4.6904 | 71 |
| 3 | 17.061 | 5.1927 | 75 |
| 4 | 14.513 | 6.0981 | 41 |
| 5 | 11.260 | 7.8513 | 39 |
| 6 | 5.568 | 15.8579 | 100. |

* * * * *